(12) United States Patent
Alt

(10) Patent No.: US 11,020,444 B2
(45) Date of Patent: Jun. 1, 2021

(54) TRANSLUMINAL DELIVERY OF VIRUSES FOR TREATMENT OF DISEASED TISSUE

(71) Applicant: SciCoTec GmbH, Gruenwald (DE)

(72) Inventor: Eckhard U Alt, Houston, TX (US)

(73) Assignee: SCICOTEC GMBH

( * ) Notice: Subject to any disclaimer, the term of this patent is extended or adjusted under 35 U.S.C. 154(b) by 0 days.

(21) Appl. No.: 15/731,467

(22) Filed: Jun. 13, 2017

(65) Prior Publication Data

US 2017/0360858 A1    Dec. 21, 2017

Related U.S. Application Data

(63) Continuation-in-part of application No. 12/766,776, filed on Apr. 23, 2010, now Pat. No. 9,675,673.

(51) Int. Cl.
*A61K 35/768* (2015.01)
*A61F 2/958* (2013.01)
(Continued)

(52) U.S. Cl.
CPC ............ *A61K 35/768* (2013.01); *A61F 2/958* (2013.01); *A61K 38/21* (2013.01);
(Continued)

(58) Field of Classification Search
CPC .. A61M 2025/1052; A61M 2025/1015; A61M 25/1011; A61M 25/00;
(Continued)

(56) References Cited

U.S. PATENT DOCUMENTS

| | | | |
|---|---|---|---|
| 4,689,041 A | | 8/1987 | Corday et al. |
| 5,306,249 A | * | 4/1994 | Don Michel ..... A61M 25/0155 |
| | | | 128/898 |

(Continued)

OTHER PUBLICATIONS

Ponnazhagan, "Parvovirus Vectors for Cancer Gene Therapy," Expert Opin. Biol. Ther. (2004) 4(1):53-64.

(Continued)

*Primary Examiner* — Theodore J Stigell
(74) *Attorney, Agent, or Firm* — Boulware & Valoir

(57) ABSTRACT

Methods are provided for treatment of cancer in a subject's body by intraluminal delivery of oncolytic viruses through a balloon catheter or alternative mechanism inserted in a blood vessel or duct leading to a target site of the cancer tissue, or for somatic cell gene therapy of single defective gene-caused other diseases or disorders by similar intraluminal delivery of non-oncolytic viruses to a target site of affected tissue and cells of the disease or disorder, wherein during delivery of the oncolytic or non-oncolytic virus, the designated vessel or duct is selectively occluded at both ends of the target site by two spaced-apart inflated balloons of the catheter to block perfusion therethrough and allow control of the volume of virus delivered to the target site so as to increase concentration and pressure of the virus thereat sufficient to enable viral penetration of an endothelial barrier of the vessel or duct without compromise thereof and into diseased cells in the vicinity of the target site toward achieving a desired therapy.

7 Claims, 3 Drawing Sheets

(51) Int. Cl.
  *A61K 38/21*  (2006.01)
  *A61M 25/00*  (2006.01)
  *A61K 48/00*  (2006.01)
  *A61M 25/10*  (2013.01)

(52) U.S. Cl.
  CPC .......... *A61K 48/0075* (2013.01); *A61M 25/00* (2013.01); *A61M 25/1011* (2013.01); *A61M 2025/1052* (2013.01); *A61M 2202/206* (2013.01); *C12N 2750/14332* (2013.01)

(58) Field of Classification Search
  CPC ........... A61M 2202/206; A61K 35/768; A61K 38/21; A61K 48/0075; C12N 2750/14332
  USPC ..................................................... 604/101.05
  See application file for complete search history.

(56) References Cited

U.S. PATENT DOCUMENTS

| | | | |
|---|---|---|---|
| 5,328,470 A | | 7/1994 | Nabel et al. |
| 5,585,254 A | | 12/1996 | Maxwell et al. |
| 5,646,185 A | | 7/1997 | Giaccia et al. |
| 5,836,905 A | * | 11/1998 | Lemelson .......... A61M 25/1011 604/21 |
| 5,922,687 A | * | 7/1999 | Mann .................. A61M 5/1452 435/440 |
| 6,489,307 B1 | | 12/2002 | Phillips et al. |
| 6,805,860 B1 | | 10/2004 | Alt |
| 7,179,456 B2 | | 2/2007 | Rommelaere et al. |
| 7,452,532 B2 | | 11/2008 | Alt |
| 9,180,281 B2 | * | 11/2015 | Gerrans ............. A61M 25/1011 |
| 2002/0055721 A1 | | 5/2002 | Palasis et al. |
| 2002/0095114 A1 | | 7/2002 | Palasis |
| 2002/0155432 A1 | | 10/2002 | Schwartz et al. |
| 2004/0076622 A1 | | 4/2004 | Studeny et al. |
| 2007/0244367 A1 | | 10/2007 | Caffey et al. |
| 2008/0249400 A1 | | 10/2008 | Golijanin et al. |
| 2008/0306570 A1 | | 12/2008 | Rezai et al. |
| 2009/0060886 A1 | | 3/2009 | Alt |
| 2018/0333563 A1 | * | 11/2018 | Agah ............... A61B 17/12136 |

OTHER PUBLICATIONS

Boekstagers et al., "Myocardial gene transfer by selective pressure-regulated retroinfusion of coronary veins," Gene Therapy, 2000, 7:232-240.

Cotmore et al., "The autonomously replicating parvoviruses of vertebrates," Adv Virus Res, 1987, 33:91-174.

Di Piazza et al., "Cytosolic activation of cathepsins mediates parvovirus H-1-induced killing of cisplatin and TRAIL-resistant glioma cells," J Virol, 2007, 81:4186-98.

Fong et al., "A herpes oncolytic virus can be delivered via the vasculature to produce biologic changes in human colorectal cancer," Am. Soc. Gene Therapy, 2009, 17(2):389-394.

Haag et al., "Highly efficient transduction and expression of cytokine genes in human tumor cells by means of in recipie parvovirus vectors; generation of antitumor responses in recipient mice," Hum Gene Ther, 2000, 11:597-609.

Hecht et al., "A phase I/II trial of intratumoral endoscopic ultrasound injection of ONYX-015 with intravenous gemcitabine in unresectable pancreatic carcinoma," Clin Cancer Res, 2003, 9:555-61.

Liu et al., "Systemic efficacy with oncolytic virus therapeutics; clinical proof-of-concept and future directions," Cancer Res, 2007, 67(2):429-432.

Makower et al., "Phase II clinical trial of intralesional administration of the oncolytic adenovirus ONYX-015nin patients with hepatobiliary tumors with correlative p53 studies," Clinical Cancer Research, 2003, 9:693-702.

Rommelaere et al., "Antineoplastic activity of parvoviruses," J Virol Methods, 1991, 33:233-51.

Sieben et al., "Killing of p53-deficient hepatoma cells by parvovirus H-1 and chemotherapeutics requires promyelocytic leukemia protein," World J. Gastroenterology, 2008, 14(24):3819-3828.

Takaoka et al., Integration of interferon-a/11 signalling to p53 responses in tumour suppression and antiviral defence, Nature, 2003, 424:516-523.

Wollmann et al., "Targeting human glioblastoma cells; comparison of nine viruses with oncolytic potential," J. Virol, 2005, 79(10):6005-6022.

* cited by examiner

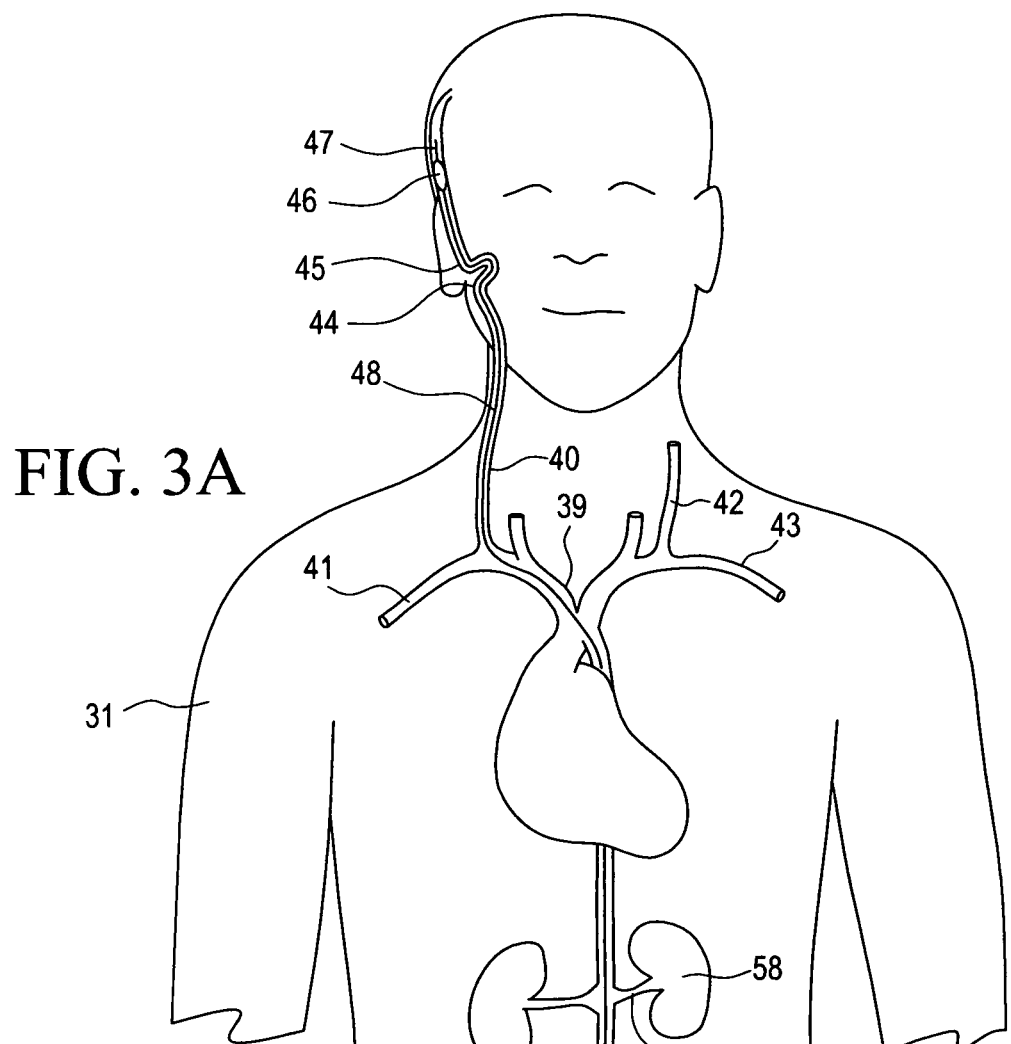
FIG. 3A
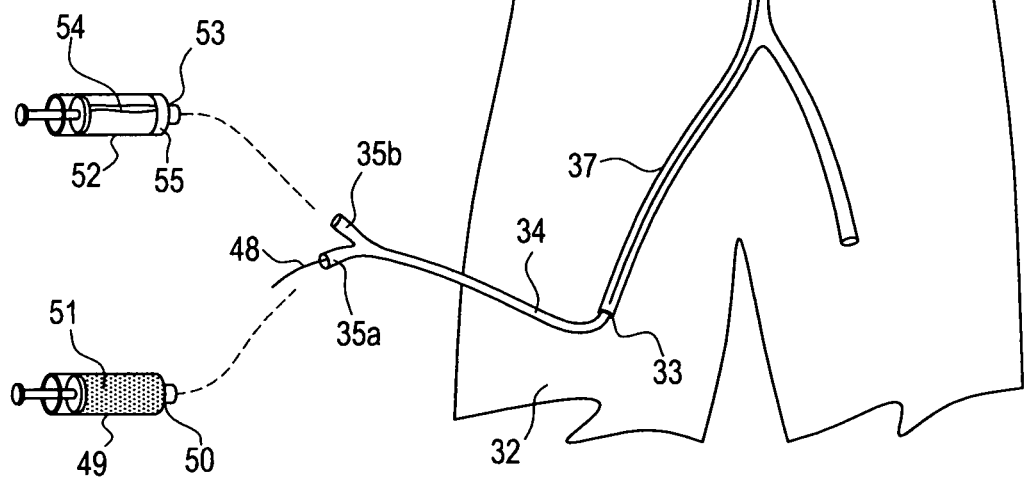
FIG. 3C
FIG. 3B

TRANSLUMINAL DELIVERY OF VIRUSES FOR TREATMENT OF DISEASED TISSUE

CROSS-REFERENCE TO RELATED APPLICATIONS

This application is a continuation-in-part of U.S. Nonprovisional application Ser. No. 12/766,776, filed on Apr. 23, 2010, now U.S. Pat. No. 9,675,673, issued on Jun. 13, 2017 ("the '673 patent"), of the same inventor herein and claims the benefit and priority of common subject matter therewith.

FIELD OF THE INVENTION

The present invention relates to improvements in compositions, systems and methods for treatment of tumors with oncolytic viruses in conjunction with supportive agents to enhance the function of the virus. The National Cancer Institute (NCI) at the National Institutes of Health (NIH) defines "oncolytic virus" as a type of virus that infects and lyses (breaks down) cancer cells but not normal cells, can occur naturally or can be made in the laboratory by changing other viruses, and certain of which are being studied in the treatment of cancer or to make it easier to kill tumor cells with chemotherapy and radiation therapy. That definition applies to the terminology "oncolytic virus(es)" as used herein.

The present invention also relates to improvements in compositions, systems and methods for treatment of non-cancerous diseases and disorders or maladies with viruses that are non-oncolytic, but engineered or designed to genetically modify cells of the subject being treated, so as to eliminate or substantially reduce the effect(s) of the disease or disorder from or on the subject. Such "non-oncolytic viruses" are defined herein as being of a type that is genetically modified to infect specific cells to remove, lyse or alter (i.e., to allay the deleterious effect of) a defective gene therein responsible for a noncancerous disease or disorder, certain of which are being studied in the treatment of the disease and disorders to cause termination or remission of the disease or disorder. These viruses are selected from a group of viruses that are able to produce among other cytokines or proteins mRNA, iRNA, shRNA, DNA or RNA on a replication stable or non-integrative manner. The viruses are also able to produce CRISPR Cas 9 (defined below) and either delete, modify or replace certain and distinct genetic information on the targeted genome.

BACKGROUND OF THE INVENTION

Since tumor cells are derived from normal cells and share basic metabolic features with those normal cells, selective destruction of tumor cells in most cases involves a balance between relative toxicity to tumor versus normal cells. Successful treatment of certain cancers has come within reach, but various tumors such as glioblastoma and pancreatic cancer, for example, remain particularly difficult to treat and are typically associated with a dire prognosis.

Pancreatic cancer is one of the most lethal of gastrointestinal malignancies, with its ranking as the fourth most frequent cause of cancer-related deaths in North America, the sixth in Europe, and the fifth in the UK. The disease has been highly resistant to available treatments. Surgical resection provides a possibility for long-term survival, but is feasible in a minority of patients only and is not without risk. In advanced disease where surgery is not an option, chemotherapy using gemcitabine or 5-FU (5-fluorouracil) in particular has been the choice, although outcomes remain modest and accompanied by high general toxicity. Malignant glioma, another of the highly lethal human cancers, when treated with conventional methods of surgery, radiation and chemotherapy, presents an average life span after diagnosis of 12-16 months.

As early as the 1800, it was observed that malignancy can suppress normal antiviral responses, and sometimes the mutations that drive tumor growth also make cells more susceptible to infection. Viral infection can thus ravage a tumor while leaving abutting healthy cells untouched. Various mid-twentieth-century experiments sought to employ viruses to infect and destroy tumors, with mixed success. In contrast, some of today's oncolytic viruses are painstakingly engineered, such as the alteration herpes virus T-VEC to drastically reduce its ability to cause herpes while making it more potent against cancer (see H. Ledford, *Nature* 526 (2015) 622-623).

A Science report of 14 May 2014 in *Business Insider* noted the story of a patient who was suffering multiple myeloma, with a grave prognosis, but experienced an "amazing" remission of her cancer after she allowed Mayo Clinic in Rochester, Minn., to infect her with a genetically engineered measles virus routinely administered as measles vaccine. The measles virus was selected because it targets cells with a specific protein common in the myeloma cells but not in normal cells. Apparently, the woman had no immunity to measles because she had never been vaccinated against it, or had lost her immunity as a side effect of treatments she had undergone previously. Otherwise, if immunity had been present the experimental treatment might have failed.

Cancer therapy using viruses or armed vector derivatives that specifically kill neoplastically transformed cells (oncolysis) is thus an approach to the treatment of certain cancers. Oncolytic viruses include certain members of a number of the virus families including herpesviridae (i.e. HSV, CMV and pseudorabies), poxviridae, adenoviridae, parvoviridae, rhabdoviridae (i.e. vesicular stomatitis virus), togaviridae (Sindbis) and picornaviridae (i.e. coxsackie virus and poliovirus).

A therapy for pancreatic cancer and other carcinomas has included delivery of an adenovirus that is selectively oncolytic for TP-53 deficient pancreatic tumor cells (see, e.g., Hecht J R, et al. "A phase I/II trial of intratumoral endoscopic ultrasound injection of ONYX-015 with intravenous gemcitabine in unresectable pancreatic carcinoma." *Clin Cancer Res* 9 (2003) 555-61). A phase II trial of intralesional administration of ONYX-015 for treatment of hepatobiliary carcinoma has also been undertaken and showed the treatment to be safe and well tolerated with modest evidence of clinical benefit (see, e.g., Malkower D. et al. "Phase II Clinical Trial of Intralesional Administration of the Oncolytic Adenovirus ONYX-015 in Patients with Hepatobiliary Tumors with Correlative p53 Studies" *Clinical Cancer Research* 9 (2003) 693). In 2005, Shanghai Sunway Biotech's genetically modified adenovirus H101, which is closely related to ONYX-015, became the first oncolytic virus to be approved by a regulatory agency for the treatment of head and neck cancer.

Human glioblastoma tumor cell lines have been found to be particularly susceptible to infection by oncolytic parvoviruses. Treatment of human gliomas with such parvoviruses by local intratumoral delivery via steriotactic surgical injection, neuronavigation targeting, and by placement of an implanted catheter connected to a low flow pump has been suggested (see, e.g., Rommelaere et al U.S. Pat. No. 7,179,456). Other viruses shown to be particularly active against glioblastomas include Vesicular Stomatitis Virus (VSV) and Sindbis virus (see, e.g., Wollman et al. Targeting Human Glioblastoma Cells: Comparison of Nine Viruses with Oncolytic Potential. *J. Virol.* 79 (10) (2005) 6005-6022).

Despite the impressive results achieved with oncolytic agents, the anti-cancer effects of such agents could be improved, particularly as to routes of administration.

The invention disclosed and claimed in the aforementioned '673 patent (from time to time referred to herein as "the '673 invention") is directed to methods and apparatuses for delivery of oncolytic viruses directly to tumors via natural fluid conduits in the body of the subject under treatment leading to or from the immediate vicinity of the tumor (i.e., transluminal or intraluminal delivery to the target), and to methods of increasing the local concentration of the viral agents at the tumor site. In one aspect, oncolytic viruses are delivered to the targeted cancer area through one or more of the vascular tree of arteries, arterioles, capillaries, post capillary venules and veins, and/or the respective ductal system of the organ that supplies fluids to or drains the cancer area. In other aspects, one or more interferons are co-administered locally together with the oncolytic viruses, or interferons are administered in conjunction with oncolytic viral therapy; for example, the interferon may be administered at several time points including one or more of before, during and after delivery of the virus.

In a preferred embodiment of the '673 invention, a method for cancer therapy is provided including delivery of an oncolytic virus by an intraluminal application through a blood vessel or duct, and, preferably, by occluding a lumen of the blood vessel or duct proximal to the location of viral egress from a delivery catheter such that concentration of viruses to the desired site can maximized. The intraluminal application of viruses through a blood vessel may be performed through an arterial or venous vessel or other fluid-transfer duct depending on the target organ. The intraluminal application may be performed in antegrade or retrograde manner.

In one aspect a balloon catheter is employed for the intraluminal application, and the occlusion of the blood vessel or duct is performed by inflating the balloon of the catheter for a time interval prescribed to increase the concentration of virus particles delivered to the local site. In other embodiments, the viral agents are delivered with pressure sufficient to cause extravasation of agent from the delivery vessel or duct and into the tissue. In one embodiment, a guide wire is introduced through the blood vessel or duct to the site, and thereafter the catheter is advanced over the guide wire until the distal end of the catheter reaches a selected point in the vicinity of the site for delivering the viruses. In one particular embodiment, the oncolytic virus is a parvovirus.

Accordingly, embodiments and methods of cancer treatment of the '673 invention involve intraluminal delivery of oncolytic viruses directly to the tumor(s) via natural fluid conduits leading to or from the immediate vicinity of the tumor, and increasing the concentration of those viruses at the tumor site as the treatment is delivered. The delivery of the virus(es) is preferably performed through a balloon catheter inserted into a blood vessel or duct constituting the natural fluid conduit of the tumor until the distal end of the catheter at which its balloon is attached and from which the virus(es) or agent(s) are to be discharged resides in the immediate vicinity and proximal to the tumor site.

In one embodiment and method of the '673 invention, the catheter has a single balloon secured at or near its distal end, a central or infusion lumen extending through the entirety of the catheter so that the virus(es) injected under relatively low pressure into the proximal end of the infusion lumen are discharged from an outlet port at the distal end of the central lumen, and distally to the single balloon when inflated via a separate inflation lumen of the catheter, but proximally to the tumor site, to obstruct fluid perfusion through the natural conduit (blood vessel or duct) at that point. The virus(es) are selected for their capacity to infect (and susceptibility to infection of) the tumor, toward achieving its ultimate destruction.

The pressure exerted on the natural endothelial lining of the vessel or duct by the virus(es) dispensed from the catheter's lumen is selectively gradually increased by their concentration or volume, and, by virtue of their distal discharge at that location and concomitant blockage of both (i) perfusion of the natural fluid (e.g., blood in the case of a blood vessel) that normally courses through the conduit (e.g., blood vessel) and (ii) retrograde loss and/or antegrade dilution of the virus(es) thereat that would occur with blood or other fluid flow in that specific location, to produce an effective extravasation pressure by which to penetrate the natural lining of the conduit and penetrate into the tumor itself, thereby delivering an effective dose of the virus(es).

In one aspect of the '673 invention, an occlusion balloon of an over-the-wire type catheter is inflated at the site of the primary injection, after the vessel has been cannulated. While the lumen of the vessel or duct is blocked, the oncolytic viruses are supplied by application through the balloon catheter over a relatively short period of time, on the order of 10 seconds to 15 minutes, for example, depending on one or more of the size of the organ, its vascularisation, the viscosity of the virus carrier, and the type of tumor being treated. Increased pressure sufficient to overcome the integrity of the lumen walls may be achieved by either more rapid delivery or increased volume over time. The viruses are injected through the inner lumen of the catheter while the balloon is inflated and the local pressure in the respective compartment is selectively increased in order to decrease potential washout of the virus.

Any cancer can be treated by the method and apparatus of the '673 invention, provided the cancer is susceptible to infection by the selected oncolytic virus and is accessible via a body vessel or duct. Examples of such cancers include tumors that are well supported by blood vessels, including pancreatic cancer, prostate carcinoma, lung cancer, renal cancer, liver cancer, lymphoma, breast cancer, and brain tumors such as glioma, medulloblastoma and meningioma.

BRIEF SUMMARY OF THE INVENTION

The principle applied in the present invention recognizes that cells or other corpuscular elements such as beads, that temporarily or permanently block the capillary blood flow, delivered by a transluminal or an intraluminal method in which the cells are injected distally from a balloon catheter inserted into a blood vessel, may cause the injected therapeutic agent, cell or virus to stick in capillaries extending from the blood vessel. This can occur whenever a high volume of corpuscular elements are being discharged in a relatively brief interval of time from the installed catheter, as corpuscular elements or cells are being forced against the flow of the bloodstream in the case of retrograde dispersal, or even with the flow of the bloodstream in the case of antegrade dispersal. This sticking of the injected elements or cells occurs because the capillary network is not capable of allowing all or even a large percentage of the cells delivered in high concentration to pass through it. As the first cells begin sticking in the capillaries, the cells following them encounter the blockage and add to it, resulting in little or no passage. Therefore, when cells, other corpuscular elements or viruses are to be injected, the pressure exerted in the immediate region of the vessel between the inflated balloon and the capillary circulation must be increased so as to force the injected substance to pass through the vessel wall and into the surrounding local tissue. In the case of the mere intraluminal delivery of a virus using a single balloon catheter without blocking the capillary outflow, the "normal" outflow along the blood vessel can only be blocked by limiting the one "escape door" (i.e., provided by the balloon inflation) in that vessel to increase the pressure.

Unlike an intraluminal delivery of cells, in cases where a virus is to be delivered, a more effective method is achieved by closing both "doors," i.e., not only the one back door with the inflated balloon, but also the front door constituting the capillary circulation. The latter will not be blocked by the virus because the virus particles are too small to cause any sticking in the capillaries that would otherwise obstruct the capillary flow. But the virus particles will suffer escape as a result of outflow from the unblocked side of the vessel or duct into which they are being delivered. Accordingly, it is a goal of the present invention to provide a method and a system for increased efficiency in delivery of viruses for local treatment of specific tissue within the body of a subject.

To that end, the present invention preferably utilizes a catheter with two spaced-apart balloons, one of which is to be positioned proximal to the target site of the malignant tumor and the other of which is to be positioned distal to the target site when the catheter has been deployed for delivery of the oncolytic or other therapeutic virus, so that the two balloons are at opposite ends of the site. The two balloons may be and preferably are coupled together by an inflation channel or lumen of the catheter running along its length from its proximal end to the inflation port of the most distally-situated balloon of the pair, and displaced radially from the guide wire lumen and the virus infusion lumen, to enable their simultaneous pressurization and simultaneous depressurization for selective contemporaneous inflation and deflation thereof.

In this way, a region (sometimes referred to herein as a compartment or a chamber) of the vessel between the two balloons is cut off (occluded) from normal circulation (of blood or other fluid depending on the nature of the vessel or duct selected for delivery of the treatment) when the two balloons are inflated. A separate port is provided for the virus infusion lumen in the catheter as an exit for the virus to the chamber of the vessel or duct formed between the two inflated balloons in the catheter. Thereby, the predetermined quantity of oncolytic virus and the body-compatible fluid in which it is contained can be injected or infused selectively into that chamber and into the affected tissue outside the vessel or duct lining to provide an effective dose for treatment of the diseased local tissue surrounding the locality of the chamber. The pressure in the formed chamber may be increased selectively by increasing the concentration of the discharged virus and its containment fluid therein, to overcome the endothelial barrier existing in the vessel wall. Owing to the small size of the virus particles, only a relatively small pressure increase is required to force the fluid containing the virus into the malignant tissue of the tumor at the target site. For example, the specific blood vessel used for the intraluminal delivery of therapy to the target site and through the endothelial barrier for infection and ultimate destruction of the tumor would typically be selected because it is supplying blood that promotes growth of a pancreatic tumor, a prostate tumor or other organ tissue tumor, such as breast cancer or liver metastasis.

For example, according to the present invention, a preferred method for treating cancer in an organ or other region of the body of a subject such as a patient comprises intraluminally delivering locally to the cancer tissue an oncolytic virus selected for its ability to infect that cancer tissue, by application of the virus(es) through an infusion lumen of a balloon catheter inserted into a natural conduit of the patient's body, such as a blood vessel or duct in direct fluid communication with a target site of the malignant tumor, much like the '673 invention. In contradistinction thereto, however, an embodiment and method of the present invention includes the use of a catheter comprising two spaced-apart inflatable balloons along its length. And, after the catheter has been fed through the blood vessel or duct to place the balloons at opposite ends of the target site of the diseased tissue (and thereby, to situate the ejection port(s) of the infusion lumen between the two balloons), the two balloons are simultaneously pressurized by delivering body-compatible inflation fluid via an inflation lumen. This action serves to hold the catheter in place, and to occlude the flow of blood or other fluid through the vessel or duct at the chamber formed between the two balloons. With the ejection port(s) thus held in confronting relation to the target site, the prescribed quantity of oncolytic virus in its containment fluid is then delivered under pressure through the catheter's infusion lumen and discharged from the ejection port(s). As the oncolytic virus is discharged, the pressure in the chamber is selectively increased by increasing the volume of fluid and quantity of virus contained therein. This forces the virus under an effective extravasation pressure through the natural endothelial barrier lining the blood vessel or duct, and thereby, into the cancerous tissue in the locality of the target site, sufficient for local delivery of an effective dose of the oncolytic virus into the cancerous tissue.

A second but less preferable method for blocking the virus distally of the target site dispenses with use of a second balloon. In this method, a single balloon catheter is positioned as before by its advancement over a guide wire initially placed in the blood vessel, and deployed with the inflated balloon situated in spaced-apart relation to the distal end of the catheter at which an ejection port is open from a central lumen running the length of the catheter and separated radially from the infusion lumen of the catheter and its discharge port from which the virus and fluid are to be discharged at the target site. Relatively fast-dissolving beads such as of gelatin or collagen composition, and of stickiness and initial size large enough to block the capillary perfusion (in a range of, say, 10 to 12 microns (μm) and not plastically compressible) are first delivered through the central lumen for ejection through the central lumen's ejection port, and bead delivery is maintained during at least the period of time over which the prescribed quantity of virus is injected in its containment fluid via the infusion lumen for discharge through the discharge port of the latter lumen. The volume of the beads delivered by ejection into the blood vessel at the distal end of the catheter is predetermined to be sufficient (e.g., a very few milliliters) to form a temporary wall blocking the discharged virus from escaping through that route distally of the inflated balloon. Appropriate attention is to be given to a compromise between (i) penetration of subsequently-delivered virus through the endothelial lining of the vessel and into the tumor tissue and (ii) allowing the capillary flow to come unblocked by the dissolving beads and to resume in relatively short order.

In all methods of the present invention, it is important to assure that blockage of blood flow is held and restored within an appropriately brief interval of time to avoid injury or death of healthy tissue for lack of perfusion.

Although oncolytic viruses are discussed in conjunction with providing cancer therapy herein, the virus selected for intraluminal delivery for purposes of the present invention need not necessarily be an oncolytic virus. Rather, it may be any virus possessing a capability to infect a subject's cells that contain a specific defective gene responsible for a disease or disorder, and to replace or disrupt the defective gene by producing therein a respective response such as a desired modification of some gene expression, by gene therapy. It is further contemplated that viruses that produce silencing RNA, shRNA, iRNA, or DNA or other proteins that exert the respectively wanted therapeutic effect and are encoded by the virus and delivered by the method of the invention. This also includes delivery of CRIPR Cas 9 produced by a replication stable or non-replication stable virus.

U.S. Pat. No. 5,328,470 to Nabel et al. ("Nabel") discloses methods of treatment of disease by site-specific instillation or transformation of cells, the methods based on the delivery of proteins by catheterization to discrete blood vessel segments using genetically modified or normal cells or other vector systems. Endothelial cells expressing recombinant therapeutic agent or diagnostic proteins are situated on the walls of the blood vessel or in the tissue perfused by the vessel in a patient. This technique is stated by Nabel to provide for the transfer of cells or vectors and expression of recombinant genes in vivo and to allow the introduction of proteins of therapeutic or diagnostic value for the treatment of diseases.

The Nabel methods require denuding of the endothelium of the blood vessel at and around the site of the vessel at which the cells are to be instilled or transformed. The denudation conditions are adjusted to achieve essentially complete loss of endothelium for cell transfers or approximately 20 to 90%, and preferably 50 to 75%, loss of cells from the vessel wall for direct infection, or, alternatively or additionally, genetic alteration/transformation of the endothelium (or endothelial cells) of the blood vessel, and thus an impaired or compromised endothelium, before instilling normal or genetically altered cells or vectors for local transformation of cells into the localized region of the vessel impairment in proximity to the region to be treated. Nabel's denuding is achieved either by mechanical trauma, by forceful passage of a balloon catheter used for the instilling, to cause scraping of inflated balloon(s) on the catheter along the vessel wall, or by chemical disruption, using proteolytic enzymes in combination with mechanical trauma, or incubation of the proteolytic enzymes or use of mild detergents. It is noteworthy that vessel impairment is highly undesirable when seeking a patient's complete recovery.

Nabel's disclosure calls for instillation of the cells using either a double-balloon or a single-balloon catheter configuration. In the double-balloon catheter configuration, the catheter has a pair of spaced-apart proximal and distal balloons along its length, with an instillation port between the two for introducing infected cells into a denuded endothelium region of the vessel in which the catheter has been inserted. The instilled cells are incubated in the dead space created between the inflated balloons for penetration into the targeted site. In the single-balloon catheter configuration, multiple ports are provided for delivery of retrovirus or transformative vectors under high pressure into the denuded segment of the vessel proximally of the inflated balloon and as a result, the vectors are subject to substantial washout. It is noteworthy that the pressure used for delivery is insufficient to force a virus of typically 100 nanometer (nm) size through the underlying cell to be penetrated having a hole of typically 10 micron ($\mu$m, or simply $\mu$) size. Moreover, even if the cell is penetrated by some virus, it is questionable whether these techniques could achieve an effective dosage within a time interval limited to avoid damage even beyond the denuded vessel endothelium to otherwise healthy tissue.

Early genetic engineering (e.g., of cells or bacteria) spawned consideration of its potential application to medicine. This was especially with respect to the possiblity of replacing or disrupting defective genes. Primary interest lay in diseases attributable to single-gene defects, such as, for example, cystic fibrosis, hemophilia, muscular dystrophy and sickle cell anemia. In gene therapy, nucleic acid polymers are delivered into a patient's cells as a drug to treat such diseases. In particular (and in the interest of simplicity of this discussion), DNA is administered to reach and enter the damaged cell(s), and thereupon either express or disrupt a protein. An initial approach was to incorporate DNA into an engineered virus to deliver the DNA into a chromosome so as to administer a gene that causes expression of a needed protein and thereby to replace or disrupt the defective gene.

Somatic cell gene therapy (SCGT) is one of the two major classifications of gene therapy. In SCGT, the therapeutic genes are transferred into any cell other than a gamete (male or female germ cell capable of uniting with one of the opposite sex in sexual reproduction), germ cell (sperm or egg), gametocyte (cell that divides to produce gametes) or undifferentiated stem cell, to produce modification(s) that affect the individual subject (e.g., recipient patient) only, and are not inherited by the patient's offspring. This class of gene therapy is applied in basic clinical research, where therapeutic DNA is integrated in the genome by incorporation into an engineered virus and delivered into a chromosome to treat disease, including current clinical trials underway focusing on severe single gene disorders such as immuno-deficiencies, hemophilia, and cystic fibrosis.

The other classification of gene therapy—germline gene therapy (GGT)—uses an approach of modifying germ cells by introducing functional genes into their genomes, resulting in all the organism's cells containing the modified gene, and hence capable of being passed along by the recipient subject to his or her progeny. Thus, for ethical and other reasons GGT remains virtually universally unapproved for application in human beings.

In one method of performing SCGT, DNA is delivered into cells through recombinant viruses typically referred to as viral vectors. The viruses replicate by introducing their genetic material into the host cell to trick the host's cellular machinery into its use as a blueprint for viral proteins. In this way, a virus's genetic material is substituted with therapeutic DNA (or RNA, in the case of some viruses), including viruses used for human gene therapy, such as retrovirus, adenovirus, lentivirus, herpes simplex, vaccinia and adeno-associated virus. The therapeutic DNA, as with genetic material (DNA or RNA) in viruses, theoretically serves as a temporary blueprint to enter the host's genome and become a permanent part of the host's DNA in infected cells, or is degraded naturally.

Various significant problems remain, however, including, for example, lack of long-term benefits, which presages the requirement that patients be subjected to multiple treatments; possibility that the treatment may provoke stimulation of the patient's immune system to attack the invading therapy; risks of toxicity, inflammatory responses, and issues with gene control and targeting, introduced by viral vectors; complications attributable to the effect of variations in multiple genes in commonly occurring disorders, such as heart disease, Alzheimer's, arthritis, and diabetes, for example; unintended result of promoting tumors; and current massive cost of treatment that uses gene therapy.

More recently, techniques involving more direct DNA editing have evolved, for example, using CRISPR in which cells are removed from the patient, a chromosome is edited by a vector (which may be a viral vector) incorporating genes therein, and the transformed cells are then returned to the patient. The acronym CRISPR stands for clustered regularly interspaced short palindromic repeats, and refers to use of segments of prokaryotic DNA containing short, repetitive base sequences. These play a key role in a bacterial defense system, forming the basis of a genome editing technology (such as CRISPR-Cas9, "Cas" referring to CRISPR-associated system) that allows permanent modification of genes within organisms. In a palindromic repeat, the sequence of nucleotides is the same in both directions. Each repetition is followed by short segments of spacer DNA from previous exposures to foreign DNA (e.g., a virus orplasmid). Small clusters of Cas genes are located next to CRISPR sequences. CRISPR/Cas9 is a simple version of the CRISPR/Cas system (a prokaryotic immune system that confers resistance to foreign genetic elements that provides a form of acquired immunity), that has been modified to edit genomes.

Thus, the methods of the present invention may be utilized to treat a disease or disorder attributable to a gene defect by gene therapy. The affected tissue of the disease or disorder may be one of an acquired or inborn disease such as HIV, immunodeficiency, cystic fibrosis, hemophilia, muscular dystrophy, or sickle cell anemia. In any of those instances, the selected virus is an engineered non-oncolytic virus having the ability to induce therapeutic RNA, mRNA, iRNA, shRNA, DNA, or CRISPR Cas9 constructs, integrated into its genome for delivery into the target site so as to induce a genetic modification that causes expression of a needed protein to modify, replace or disrupt the defective gene for treatment of the disease or disorder.

Therefore, it is emphasized that non-oncolytic viruses may be used to treat single gene diseases and disorders, such as including those mentioned above, that are not cancers. And although methods of the treatment employ non-oncolytic viruses engineered according to the single gene non-cancerous disease or disorder of interest, those viruses are applied using the same or substantially the same methods as are used for delivery of oncolytic viruses for treatment of cancers; that is, in its broadest aspect, the present invention resides in methods of delivery of an agent or virus selected (e.g., engineered) for its ability to infect defective cells of affected tissue in the body of a subject so as to allay the defect therein while leaving normal cells unscathed, and without removing or otherwise injuring the endothelium of the lining of the vessel or duct through which the virus is administered. Absent use of the methods of the invention, including a buildup to effective extravasation pressure for penetration, most viruses are too large to cross the barrier of the normal endothelial lining of the blood vessels and extravasate in sufficient concentration in defective cells of targeted affected tissue to achieve safe and effective treatment.

A broad aim of the present invention is to provide a method for treating a disease or disorder in the body of a subject, comprising the steps of occluding a blood vessel or duct of the body bounding a target site of defective cells of affected tissue of the disease or disorder by introducing into the vessel or duct a catheter with two spaced-apart balloons having at least one discharge port with an opening therebetween coupled to an infusion lumen of the catheter, and thereafter inflating the two balloons so as to create a chamber therebetween in which perfusion through the vessel or duct is blocked at the target site and the opening of the at least one discharge port confronts the target site within the chamber; delivering an effective dose of a selected cell defect-correcting agent contained in a body-compatible fluid carrier under pressure into the chamber through the opening via the infusion lumen by controlling the volume and thereby the pressure of the agent-fluid combination in the chamber so as to reach an effective extravasation pressure sufficient to force the effective dose of the agent through the natural endothelial barrier at the lining of the vessel or duct, without inflicting damage thereto, to penetrate and induce the desired therapeutic effect in cells of the affected tissue at the target site.

A related aim of the invention is to provide the latter method wherein the selected cell defect-correcting agent is one or more substances in the group consisting of viruses, unmodified or engineered exosomes, microvessicles, cytotoxic and cytostatic agents including interferons or chemical compounds inducing cytotoxic/static effects, and substances modifying the immune tolerance including negative co-stimulators and check point inhibitors.

Another aim of the present invention is to provide a method for treating a disease or disorder in the body of a subject by delivering effectively and with high concentration a selected virus locally to affected tissue at a target site of defective cells of the body responsible for the disease or disorder to be treated, the method including selecting the virus for its ability to infect the defective cells in the affected tissue so as to allay the defect therein while leaving normal cells unscathed; selecting a balloon catheter sized for advancement to the target site through a blood vessel or fluid duct of the subject's body in direct fluid communication with the target site, and having a discharge port of an infusion lumen situated between two spaced-apart inflatable balloons coupled by an inflation lumen of the catheter; advancing the catheter through the vessel or duct to position its distal end such that the target site is located between the two balloons, and inflating both balloons through the inflation lumen to maintain the catheter so positioned with the discharge port confronting the target site, thereby forming an open space encompassed by the lining of the vessel or duct, the outer surface of the catheter, and confronting surfaces of the two inflated balloons and blocking normal perfusion through the vessel or duct within that space; transluminally infusing therapeutically effective doses of the virus in containment fluid for discharge into said space through the infusion lumen and its discharge port; and selectively increasing pressure of the discharged virus by increasing the volume of fluid containing the virus in said space, to force the virus under an effective extravasation pressure through the natural endothelial barrier of the lining of the vessel or duct within said space, without removing or otherwise injuring the barrier, and into the defective cells of the affected tissue at the target site, sufficient for delivery of the effective doses of the virus thereto.

A related aim is to provide such a method for treating cancer, in which the affected tissue is a malignant tumor, the selected virus is an oncolytic virus, and each of the therapeutically effective doses of the virus is contained within a pharmaceutically acceptable fluid carrier constituting the containment fluid.

A related goal is to provide such a method wherein the disease or disorder to be treated is attributable to single-gene defects for treatment by somatic cell gene therapy, the affected tissue is one of an immunodeficiency, cystic fibrosis, hemophilia, muscular dystrophy, and sickle cell anemia, and the selected virus is an engineered non-oncolytic virus having incorporated therein therapeutic DNA integrated into its genome for delivery into a chromosome so as to administer a gene that causes expression of a needed protein and thereby replace or disrupt the defective gene, using the delivery method of the invention for cell penetration.

A further aim of the invention is to provide a method for treating a disease or disorder in the body of a subject, the method including the steps of selecting a balloon catheter with two distally spaced-apart inflatable balloons coupled by an inflation lumen thereof for simultaneous inflation or deflation, and with an infusion lumen having a discharge port situated between the two balloons; feeding the balloon catheter transluminally into a vessel or duct of the body in direct fluid communication with affected tissue of the body containing defective cells responsible for the disease or disorder to be treated, until the two balloons are positioned at opposite ends of a target site of the affected tissue; inflating the two balloons through the inflation lumen while injecting through the infusion lumen of the catheter a body-compatible fluid containing a predetermined quantity of a virus selected for its ability to infect the defective cells so as to allay the defect therein while leaving normal cells unscathed, to discharge the quantity of virus in the fluid from the discharge port into a chamber at the target site formed by the space encompassed by the lining of the vessel or duct and the outer surface of the catheter between the surfaces of the two inflated balloons; and selectively increasing pressure of the discharged virus and fluid in the chamber to force the virus under an effective extravasation pressure through a barrier presented by the endothelial lining of the vessel or duct, without removing or otherwise injuring the endothelial lining, for delivery of an effective dose of the virus into the defective cells of the affected tissue at the target site.

Still another aim of the invention is to provide a method for treating a disease or disorder in the body of a subject, including selecting a balloon catheter with an inflatable balloon spaced from the distal end and coupled to an inflation lumen of the catheter, and with an infusion lumen having a discharge port situated distally of the balloon and proximally of its distal end, and a separate central lumen having an outlet port at the distal end of the catheter; feeding the balloon catheter transluminally into a vessel or duct of the body in direct fluid communication with affected tissue of the body containing defective cells responsible for the disease or disorder to be treated, until the balloon is positioned at one end and the outlet port is positioned at an opposite end of a target site of the affected tissue; inflating the balloon through the inflation lumen and dispensing body-compatible soluble beads through the central lumen for ejection from the outlet port, and injecting through the infusion lumen of the catheter a body-compatible fluid containing a predetermined quantity of a virus selected for its ability to infect the defective cells so as to allay the defect therein while leaving normal cells unscathed, to discharge the quantity of virus in the fluid from the discharge port into a chamber at the target site formed by the space encompassed by the lining of the vessel or duct and the outer surface of the catheter between the surface of the inflated balloon and the surface of a wall presented by the beads ejected from the distal end; and selectively increasing pressure of the discharged virus and fluid in the chamber to force the virus under an effective extravasation pressure through a barrier presented by the endothelial lining of the vessel or duct, without removing or otherwise injuring the endothelial lining, for delivery of an effective dose of the virus into the defective cells of the affected tissue at the target site.

Yet another goal of the invention is to provide a method for treating a disease or disorder in the body of a subject, comprising the steps of occluding a blood vessel or duct of the body bounding a target site of defective cells of affected tissue of the disease or disorder with two spaced-apart balloons of a balloon catheter inflated to create a chamber therebetween at the target site in which normal perfusion through the vessel or duct is blocked, delivering an effective dose of a selected agent contained in a body-compatible fluid carrier under pressure into the chamber in the blocked portion of the vessel or duct, and controlling the volume of selected agent and its containment carrier delivered into the chamber and thereby the pressure therein so as to reach an effective extravasation pressure sufficient to force the effective dose of the agent through the natural endothelial barrier lining the vessel or duct in the chamber, without inflicting damage thereto, to penetrate and induce the desired therapeutic effect in cells at the target site.

In practice, the two-balloon catheter is preferably of diameter size about four French (1.3 millimeters, mm), for example. Balloon catheters are available or readily produced with up to 3 or 4 channels (lumens), including a proximal one at approximately the diametric center of the catheter that extends end to end of the catheter's length to accommodate an initially placed guide wire over which the catheter is to be advanced. Another is an inflation lumen for the balloons, and yet another is an injection (infusion, or delivery) lumen for the virus and fluid to be discharged from a port or ports between the two balloons.

A two-lumen catheter might be used, in which the central lumen could accommodate the guide wire and also enable injection of the fluid containing the virus. The latter objective may be achieved by positioning a membrane, such as silicon-based, at the very end of the catheter tip or even anywhere beyond the injection port(s), suitable for passage of the guide wire (by penetration or by hinged movement) but automatically closed when the guide wire is removed following proper placement of the catheter in the blood vessel, so as to allow the pressure increase at the port and the chamber or compartment between the two inflated balloons. In such a way, the compartment or segment between the "doors" may be pressurized with the delivery of virus and fluid therein to force the virus through the endothelial barrier and into the tumor tissue.

BRIEF DESCRIPTION OF THE DRAWINGS

For a more complete understanding of the present invention, including its various features and advantages, reference will now be made to a detailed description of the invention in conjunction with the accompanying figures, in which:

FIG. 3A is a transparent front view of a subject illustrating an exemplary procedure for injecting a prescribed quantity of virus contained in body-compatible fluid into the cerebral circulation of a patient, and FIGS. 3B and 3C are companion simplified views of syringes used in the course of such procedure.

Figure 1A:
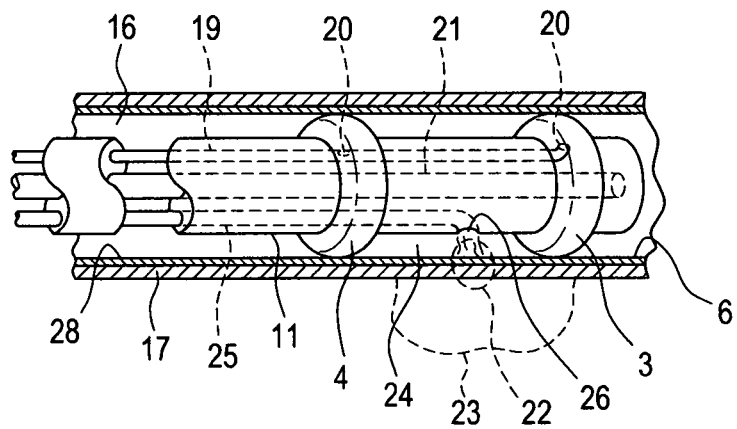
FIG. 1A is a simplified partial cut away cross-sectional view of a preferred embodiment of a two-balloon catheter positioned-in-place in a vessel or duct of the body, to be used in performing methods of infusing selected infecting viruses, whether engineered or unmodified, into defective cells of affected tissue attributable to a disease or disorder suffered by the subject.

It should be noted at the outset that the figures are not intended to be to scale, nor to do more than serve as a visual aid to the description. In those figures representing the human body or body parts, certain components may be exaggerated relative to others for the sake of emphasis or clarity of the respective accompanying description. Also, it will be understood that the individual elements of the virus delivery system are not necessarily intended to reflect the specific shape(s) of those elements. Individual elements common to several Figures are in most instances designated by the same or closely related reference number.

DESCRIPTION OF PRESENTLY PREFERRED EMBODIMENTS AND METHODS

Certain embodiments of the present invention are directed to improvements in the method(s) and apparatus(es) utilized for prior local and regional delivery techniques, by administering viral agents with a multi-balloon catheter of various advantages.

In the instance of treating malignant tumors, for example, the methods disclosed herein exploit the abnormal structure of tumor vasculature. Although small clumps of nascent tumor cells are able to acquire oxygen and nutrients by diffusion, solid tumors require formation of new blood vessels for growth. The tumor thus rapidly induces the formation of a dedicated vasculature able to support progression. However, this vasculature features structural and functional abnormalities including decreased vessel density, heterogeneous microvessel distribution, increased sinusoids, dead ends and arterio-venous anastomosis, and vessels having incomplete basement membranes and absence of smooth muscle. In short, tumor vasculature is characterized by immature, highly-permeable, chaotic vessels with heterogeneous blood flow. The present invention, in its embodiments and methods for treating cancer, applies pressure-mediated delivery of oncolytic viruses to the tumor via vessels and ducts leading to the body tissue bearing the tumor.

Use of a balloon catheter provides several advantages in the treatment of cancers with oncolytic infecting viruses, and, as will be more fully understood from the detailed description herein, in the treatment of other diseases and disorders with prescribed infecting viruses, whether engineered or natural. These advantages include selectively local increases in viral concentration, isolation of the delivered viruses from normal fluid flow pressures in the target tissue in order to increase contact time and minimize interaction with systemic antibodies, and pressure-mediated delivery which allows the viruses to transit the cellular boundary of delivery ducts and vessels to become trapped in spongy fluid conduits characterizing, in some cases, the affected tissue. In one embodiment, the virus is applied in a delivery solution having increased viscosity in order to increase the pressure of delivery and to minimize washout of the viruses from the targeted site in the vessel or duct in which the balloon catheter is installed for delivery of the viruses to that site.

Procedures disclosed herein are particularly directed to the requirements of the clinical practice of interventional medicine, and thus follow the principle that only those approaches that are both (a) relatively easy to perform, with little or no risk but of potentially significant benefit to the patient, and (b) highly cost effective, are likely to be routinely applied in everyday medicine. The approach provided is based on an appreciation by the applicant that biological agents such as viruses are preferably delivered in local concentration to the targeted site, and that such agents need a certain amount of contact time to adhere and migrate from a vascular or ductal bed into the target site.

In preclinical studies, adhesion of the injected viruses and their migration past the endothelial bather of the vessel or duct by which they are to be intraluminally delivered, and into the defective cells responsible for or attributable to the disease or disorder under treatment, may be confirmed by observation after several hours/days of frozen sections using light microscopy and, if desired, by electron microscopy. In addition, a green fluorescence protein (GFP) or other marker may be used to aid the observation by introduction of the GFP gene into the viral genome with detection of expressed protein by fluorescence microscopy. Alternatively or in addition, the viruses can be grown in radioactive medium to label their RNA or DNA with radioactive tags that may enable a gross estimate of the concentration delivered to the specific targeted tissue. Further methods that are more sensitive include detection of viral DNA/RNA by molecular methods including RT-PCR.

The disclosed approach is suitable for delivery of any virus that naturally or by engineering is able to preferentially infect and kill or allay (i.e., subdue or reduce the intensity or severity of) the deleterious effect of defective cells, whether cancerous or containing defective genes attributable to or responsible for other disease or disorder. To date oncolytic viruses have been identified or developed in members of both DNA and RNA virus families including herpesviridae (i.e. HSV, CMV and pseudorabies), poxviridae, adenoviridae, parvoviridae, rhabdoviridae (i.e. vesicular stomatitis virus), togaviridae (Sindbis) and picornaviridae (i.e. coxsackie virus and poliovirus).

In one embodiment of the invention for treating cancers, the oncolytic virus is a parvovirus including wild-type autonomous or modified replication competent derivatives thereof as well as related viruses or vectors based on such viruses or derivatives. Parvoviruses are small (25-30 nanometer (nm)) non-enveloped particles containing a 5.1 kb single-stranded DNA genome from which two nonstructural (NS1, NS2) and two capsid (VP1, VP2) proteins are expressed (see, e.g., Cotmore S F and Tattersall P. "The autonomously replicating parvoviruses of vertebrates" *Adv Virus Res* 33 (1987) 91-174). Some autonomous parvoviruses belong to the category of oncolytic viruses (see, e.g., Rommelaere J, Cornelis J. "Antineoplastic activity of parvoviruses" *J Virol Methods* 33 (1991) 233-51). Several members of the parvovirus genus (H-1PV, MVM, LuIII), whose natural hosts are rodents, are presently under consideration for cancer gene therapy applications due to their failure to transform host cells, capacity for asymptomatic infection of humans, and ability to preferentially propagate in (oncotropism) and kill (oncolysis) neoplastically transformed cells (see, e.g., Haag A, et al. "Highly efficient transduction and expression of cytokine genes in human tumor cells by means of autonomous parvovirus vectors; generation of antitumor responses in recipient mice" *Hum Gene Ther* 11 (2000) 597-609).

Parvovirus H-1PV has the unique advantage of triggering a distinct death process, at least in brain and some other tumors, namely the cytosolic relocation and activation of lysosomal proteases (cathepsins) (see, e.g., Di Piazza M, et al. "Cytosolic activation of cathepsins mediates parvovirus H-1-induced killing of cisplatin and TRAIL-resistant glioma cells" *J Virol* 81 (2007) 4186-98). As a further advantage, MVMp and H-1PV viruses have been shown to exert oncosuppressive activities in vivo, i.e. they are able to inhibit the formation of spontaneous, chemically or virally induced tumors in laboratory animals. Suitable parvoviruses for purposes of the present invention in cancer treatment include but are not limited to rodent parvovirus species H-1 PV, LuIII virus, various strains of Minute virus of mice (MVM) (recently renamed mice minute virus (MMV)), including MVPi and MVPp, Mouse parvovirus (MPV), Rat minute virus (RMV), Rat parvovirus (RPV) or Kilham Rat virus (RV).

The oncolytic (or non-oncolytic, for treatments of diseases or disorders other than malignancies) viruses are delivered in an effective dose and combined with a pharmaceutically acceptable carrier. An "effective dose," as used herein, refers to amounts of the active ingredients that are sufficient to affect the course and the severity of the disease, leading to the reduction or remission of such pathology. An "effective dose" useful for treating and/or preventing diseases or disorders addressed by the present invention may be determined using methods known to those ordinarily skilled in the art. Such methods and background art are disclosed for example by Marchini et al. in U.S. patent application Ser. No. 14/355,691 published Oct. 16, 2014. The terminology "pharmaceutically acceptable" is used herein to encompass any carrier that does not interfere with the effectiveness of the biological activity of the active ingredients and that is not toxic to the patient to whom it is administered. Examples of pharmaceutically acceptable carriers suitable for selection under those premises are well known in the art and include phosphate buffered saline solutions, water, emulsions, such as oil/water emulsions, various types of wetting agents, sterile solutions, etc. Such carriers are or can be formulated by conventional methods and administered to the subject with an effective dose of oncolytic virus(es) contained therein.

As used herein, "effective extravasation pressure" means a pressure sufficient to exceed the normal fluid pressure of a given lumen and cause fluids to be forced between cells forming the lumen walls and thereby overcome the endothelial barrier consisting of endothelial cells and the basal membranes of the vessel or duct, and sufficient to penetrate and enter the targeted cells themselves. Because of the abnormal vasculature of tumor tissue, tumor tissue is particularly susceptible to pressure-mediated delivery. In one embodiment, the oncolytic virus formulation includes a marker such as a dye or radiomarker that can be visualized during administration with adjustment of extravasation pressure to assure effective perfusion of the administered agent into the tumor and immediately surrounding tissue. In one embodiment, the marker is a nuclear tracer such as Tc-99 or a MRI sensitive agent such as Gadolinium or derivatives thereof, and small superparamagnetic particles such as iron oxide nanoparticles. Typically, a change in pressure of 20 mm Hg is sufficient to overcome the endothelial pressure in normal tissue. Visualization of the delivery process permits adjustment of delivery pressure to achieve desired perfusion of the tumor tissue.

The essence of the present invention pertains to methods of delivery of the therapeutic substances, and not only to methods of delivery of oncolytic or non-oncolytic viruses, but also to delivery of other agents selected to enhance the effectiveness of treatment utilizing those very same methods of the delivery. Non-limiting examples of those other agents include substances such as natural or engineered exosomes, microvessicels, cytotoxic and cytostatic agents such as interferons or chemical compounds inducing cytotoxic/static effects or substances modifying the immune tolerance such as negative co-stimulators or check point inhibitors. For these therapy-enhancing agents, the same principle applies, that is, of overcoming without harming the endothelial barrier lining a blood vessel or fluid duct in fluid communication with defective cells of tissue affected by the manifestation of the disease or disorder to be treated, and thence, penetration of the cells of the affected tissue by controlled application of an extravasation pressure effective within a compartment or chamber of the vessel or duct blocked against perfusion therethrough and in which a target site of the affected tissue is present to selectively enhance delivery and concentration so as to force the therapy-enhancing agents and selected virus(es) from the compartment in dosages effective to alleviate the defect in the penetrated cells.

These therapy-enhancing agents may be delivered either together with the virus or delivered completely independently thereof. Transluminal or intraluminal delivery of the infecting viruses with or without therapy-enhancing agents through a blood vessel may be performed through an arterial or venous vessel in cardiovascular communication with the designated target site of affected tissue. Non-oncolytic viruses are typically selected for delivery by virtue of their capacity to infect the defective cells, and their having been engineered (or in some instances, natural propensity) to supply or remove or overexpress or suppress certain cellular genes and connected protein expression, thereby altering the function of the cells.

A balloon catheter is employed for the intraluminal application of infecting viruses for reasons noted earlier herein and especially reasons of simplicity, effectiveness, and widespread use in a number of diagnostic and therapeutic procedures, and is therefore in keeping with the clinical practice of interventional medicine. In a preferred embodiment of the method and system of the present invention, the catheter is of a two-balloon type, wherein the two balloons are spaced-apart from or near the vicinity of the catheter's distal end. Occlusion of the blood vessel or duct to prevent or to stem perfusion of the fluid normally carried therethrough is performed by inflating the catheter's balloons simultaneously for a time interval prescribed to increase the pressure, concentration and effectiveness of oncolytic agents (in the case of cancer treatment, or of selected non-oncolytic viruses in the case of treatment of other diseases and disorders) delivered to the targeted body tissue to be treated.

Use of the two-balloon catheter allows the desired delivery of therapeutic viruses, agents and substances to be achieved by effective extravasation pressure as defined above. Typically, bolus injection will result in pressure in excess of the normal range of fluid pressure within the respective artery, vein or duct into which the balloon catheter has been advanced for purposes of treatment of the disease or disorder of interest. The effective extravasation pressure is achieved by controlling the volume of virus and its fluid carrier infused into the aforementioned compartment or chamber created by inflating both balloons when positioned with the target site therebetween, and may be expected to force fluid including the virus into the intercellular space between cells lining the blood vessel or duct.

Whether employed for treatment of malignant tumors or of other diseases or disorders, the delivery method applies pressure-mediated viral delivery of either oncolytic viruses that selectively infect, replicate in and destroy tissue (in the case of tumors), or non-oncolytic viruses that selectively infect and destroy or allay the effects of defective cells (in the case of other diseases or disorders), through a blood vessel or duct or a tree thereof in the subject's body, and into defective cells of targeted tissue of the tumor or other disease or disorder navigable therethrough in such a way as to assure that regional high concentrations in effective dosage of the selected virus(es) are able to penetrate the endothelial barrier of the vessel or duct lining without injury or compromise thereof.

Emerging clusters of tumor cells, for example, which may include millions of cells, are too small to be individually perceived and targeted by intra-tumoral injection, and thus, such injection of oncolytic viruses is very likely to be ineffective to permit exposure of the viruses to all of the foci of tumor cells in a targeted organ or region of body tissue. It is important to recognize that the selected oncolytic (or non-oncolytic, as the case may be) virus in its pharmaceutically acceptable carrier can be applied broadly in the affected region of the body while localizing the viruses in the area of the affected tissue and cells for an interval of time (as in the aforementioned compartment or chamber created by the inflated balloons at the target site) sufficient to achieve an effective extravasation pressure and thereby, attachment of and infection by an effective dose of the viruses. Tumor vasculature and the endothelial lining of vascular and ductal structures in a tumor are abnormal, but these abnormalities can be overcome to advantage by techniques known to those of skill in the art.

In various methods of deployment of the system for practicing the methods of the invention, a guide wire is first introduced through the blood vessel or duct to the target site of the body tissue to be treated, and thereafter the balloon catheter is advanced either manually or mechanically driven over the guide wire until the distal end of the catheter reaches a selected point in the vicinity of the affected body tissue that places a target site for treatment between the two balloons (when inflated) for delivering the virus and its carrier thereto.

Reference will now be made to the accompanying figures in describing exemplary methods and systems for viral delivery. The description of the figures may refer in some instances to virus delivery for destroying a tumor, and in other instances to virus delivery for altering or allaying the effective of defective cells in affected body tissue of another disease or disorder, but it is to be understood that the basic method of virus delivery is the same or substantially the same in either case. That is, the only significant differences may be the type of virus employed in the treatment, and that virus' effect on the affected tissue or cells thereof.

In practice, a preferred method of the present invention utilizes a two-balloon catheter of length and diameter to accommodate its threading through the vasculature or ductwork necessary to reach the body tissue designated for treatment, and the catheter having multiple lumens therein to accommodate delivering multiple materials therethrough. For example, a two-balloon catheter having diameter size of about four French (equivalent to about 1.3 millimeters, mm), and a balloon diameter of about 2.54 centimeters (cm) when inflated (i.e., the same for each balloon) might be selected, for a snug fit and suitable blockage of perfusion in the vessel. Balloon catheters are available or readily produced with up to 3 or 4 channels (lumens), including a proximal lumen at or near the diametric center of the catheter and extending through the entire length of the catheter to accommodate its being advanced over a guide wire initially inserted into the vessel or duct. Another channel to be provided in the instant embodiment is an inflation lumen for selective inflation or deflation of both balloons simultaneously, and yet another channel as an injection or infusion (delivery) lumen for the virus and its carrier fluid to be discharged from a port or ports between the two spaced-apart balloons when positioned with the target site therebetween, one balloon located at or very near the catheter's distal end (i.e., referred to from time to time herein as the more distal balloon) and the other situated proximally thereto (i.e., referred to from time to time herein as the more proximal balloon), spaced about 1 to 2 inches apart, for example.

An alternative, but less preferred method utilizes a single balloon catheter, to be advanced through the vessel or duct path leading to the target site of the affected tissue to be treated, over the initially inserted guide wire, as in the case of the two-balloon catheter. In this alternative method, however, the single balloon is situated as was the more proximal balloon of the two-balloon catheter. One or more discharge ports of the injection lumen from which the virus and carrier fluid are to be discharged is disposed distally of the single balloon and proximally of the distal end of the catheter so that when the catheter is fully advanced (for delivery of the treatment) in the vessel or duct, the target site is located between the balloon and the distal end of the catheter substantially opposite the discharge port(s). Blockage of normal perfusion through the vessel or duct using this single balloon embodiment is established in the manner described below. The catheter is provided with three lumens, including the previously-mentioned injection or infusion lumen, and as well, an inflation/deflation lumen for the single balloon, and a central lumen extending the entire length of the catheter.

The central lumen of this alternative embodiment provides two purposes, viz., (1) it allows the catheter to be advanced over the guide wire, after which the guide wire is removed through the proximal outlet of the central lumen, and (2) the now-open central lumen is utilized to inject under pressure a multiplicity of relatively fast-dissolving beads such as of gelatin or collagen composition therethrough for ejection from the central lumen's open port at the distal end of the catheter. The beads are formed or selected to be of an initial size large enough (in a range of, for example, 10 to 12 microns ($\mu$m) and not plastically compressible) to form a wall as they are ejected from the distal end of the catheter so as to temporarily block perfusion through that portion of the vessel or duct between the inflated balloon and the bead-formed temporary wall. The beads should be delivered through the central lumen for at least a period of time before and over which the virus is forced under pressure through the infusion lumen and discharged therefrom through the discharge port, to maintain the integrity of the formed wall and avoid virus escape therethrough during that period. The volume of the beads ejected into the blood vessel or duct should be sufficient (e.g., a very few milliliters) to not only block perfusion therethrough but also to prevent the virus from escaping through that route from the chamber bounded by the inflated balloon, the bead wall and the outer surfaces of the catheter and the lining of the vessel or duct wall. As always, when perfusion of blood is being blocked intentionally, appropriate attention must be given to a compromise between (i) penetration of the delivered virus through the lining endothelium and into the infected cells of the affected tissue and (ii) allowance of the capillary flow to resume before damage to or cell death of healthy tissue.

Referring now to FIG. 1A, a partial cut away cross-sectional view of a positioned-in-place preferred catheter 11 for performing the virus delivery method of the invention has two balloons spaced-apart along its length, one of which is the more distal balloon 3 and the other of which is the more proximal balloon 4. In this Figure, the catheter is depicted after having been advanced at its distal end to a designated location 6 in a blood vessel or duct 16 (only the vessel wall 17 being shown in a lengthwise cross-section through its central axis, for the sake of clarity and simplicity), and the two balloons inflated for a snug fit and perfusion blockage in the vessel. Simultaneous inflation of the two balloons is effected by infusing a suitable biocompatible fluid through an inflation lumen 19 having an outlet port 20 into each balloon. The catheter also has a central lumen 21 open at each of its proximal and distal ends for passage over a guide wire (not shown) that was initially inserted into the vessel 16 to at least the designated end point 6, and after the catheter has been advanced to the appropriate position, as viewed by applicable means such as fluoroscopy, the guide wire is removed.

The positioning of the catheter 11 in the vessel or duct is intended to place a designated target site 22 of the affected tissue attributable to or responsible for the tumor 23 or other disease or defect, between the two balloons 3, 4 within a space forming a chamber 24 bounded by the opposing surfaces of the two balloons, and the surface of the catheter and the inner surface of the vessel wall between the balloons. After the proper positioning has been achieved, the balloons are deployed by inflation thereof to block perfusion through the chamber. Then, an appropriate volume of the selected infecting virus constituting an effective dose within its pharmaceutically acceptable carrier, is proximally infused through the catheter's infusion lumen 25. The infused virus and carrier may be in the form of a stream or a bolus, and the infusion is performed under pressure for ejection from a discharge port (or ports) 26 of lumen 25 into the chamber 24. The pressure of the virus and carrier within the chamber is controlled by the volume and concentration of the virus/fluid delivered therein, as well as the time interval over which those elements are maintained within the chamber. This control is maintained so as to force the effective dose of the virus under an effective extravasation pressure through the natural endothelial barrier at the lining 28 of the vessel or duct wall 17 and into the infected cells of the affected tissue. It is noteworthy that penetration of the endothelium of the vessel's lining is achieved without damage, denuding or other compromise to or of that barrier or to the vessel lining itself. This assures that the desired "cure," remission or revision will not bring about an equally or other deleterious outcome as the original disease or disorder sought to be treated.

Figure 1B:
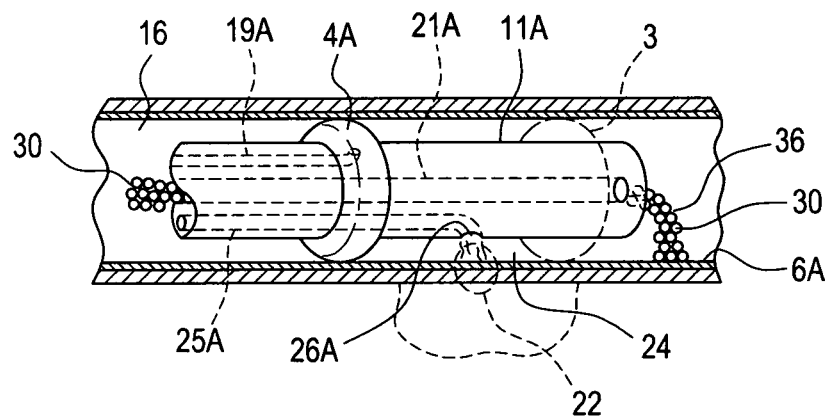
FIG. 1B is a simplified partial cut away cross-sectional view of an alternative, but less preferred embodiment of a balloon catheter positioned-in-place as was the embodiment of FIG. 1A, to be used in performing methods of infusing such selected infecting viruses into defective cells.
Figure 2:
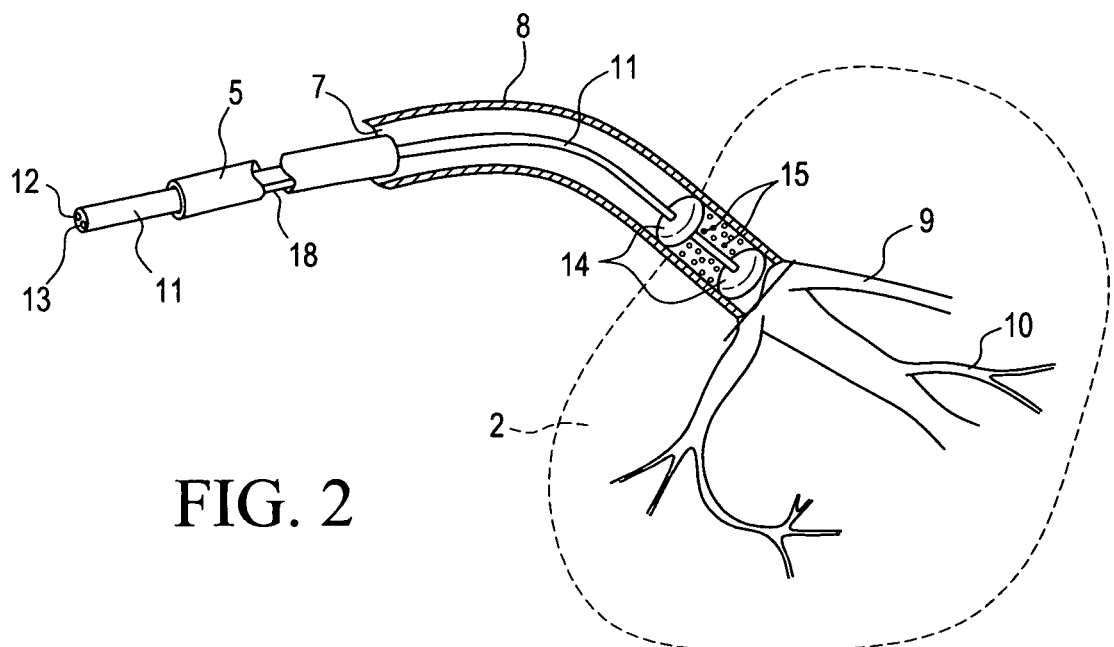
FIG. 2 depicts a balloon catheter of the type shown in FIG. 1A, inserted into an arterial tree leading to targeted affected tissue in the body of a subject for administering a selected infecting virus into tissue of a malignant tumor or into affected tissue attributable to a different disease or disorder.

Referring now to the also partial cutaway and cross-sectional view of FIG. 1B, an alternative, but less preferred embodiment than that of catheter 11 of FIG. 1A, is utilized for performing the method of the present invention with a single balloon version designated 11A. Catheter 11A is shown in a portion of a vessel or duct 16 of the subject's body selected for viral delivery. The single balloon 4A of this catheter is situated as was the more proximal balloon of the two-balloon catheter. A second more distal balloon 3, not present in this embodiment, would have been located on the catheter as shown by dotted lines. As with catheter 11, the catheter 11A has three lumens, designated here as 19A, 21A and 25A, but unlike the embodiment of FIG. 1A, inflation lumen 19A extends only as deeply as and into balloon 4A for inflation thereof, and central lumen 21A is used for two purposes.

First, the central lumen accommodates removal of a guide wire (not shown) that had been inserted initially into duct 16 to a point 6A beyond that of point 6 to which the distal end of two-balloon catheter 11 was advanced, for a reason that will become clear presently. After the catheter 11A is advanced over the guide wire to position its distal end short of point 6A, the guide wire is withdrawn from the proximal outlet of the central lumen 21A, leaving that lumen open as an outlet at its distal end. The infusion lumen 25A extends into catheter 11A only sufficiently deeply to situate its discharge port 26A (more than one of which may be spaced circumferentially on the catheter at that depth so as to allow greater infusion but not so many as would sacrifice the integrity of the catheter threat) approximately midway between balloon 4A and the catheter's distal end. And the positioning of the catheter 11A within duct 16 for deployment and inflation of balloon 4A is made to place the discharge port(s) 26A substantially directly opposite a target site 22 of the affected tissue to be treated.

After such positioning of the catheter and deployment of its balloon, a multiplicity of relatively fast-dissolving beads 30 such as composed of gelatin, mannitol, dextrose, sorbose, sucrose, or collagen (see, for example, U.S. Pat. No. 4,827, 940) are injected under low pressure through now-open central lumen 19A from its proximal inlet to its distal outlet for ejection therefrom. As the beads, which are selected to have an initial size in a range of, for example, 10 to 50 µm and of low compressible consistency, emerge in large numbers from the distal outlet and stick together in an outward flow large enough to form a temporary wall 36 slightly beyond the distal end of the catheter 11A at the capillary level. After a time interval sufficient to allow wall 36 to be established to block perfusion through the duct and form chamber 24, but before the wall begins to disintegrate as the result of dissolution of beads by which it was formed, i.e., an interval of about one to a few minutes, a predetermined volume of the pharmaceutically acceptable fluid carrier containing an effective dose of the selected infecting virus (and therapy-enhancing agent, if desired) is driven under increasing pressure through infusion lumen 25A and from discharge port(s) 26A. The discharge is monitored and largely maintained by controlling its volume and pressure within chamber 24 until it builds to the desired effective extravasation pressure sufficient for the virus to penetrate the endothelial barrier presented by the lining 28 in the vessel or duct wall 17, without damage thereto, and into the defective cells of the affected tissue at and around the target site 22.

A sufficient volume of beads 30 (e.g., typically consisting of only a few milliliters, such as 2 to 5 ml) is selected for ejection into the blood vessel or duct to form the temporary wall 36 and thereby block perfusion therethrough, as well as to avoid escape of the virus/carrier fluid from the chamber 24 except for penetration of vessel wall 17 without denuding its lining, and into the affected tissue and its cells thereunder. Chamber 24 occupies the same space as described above for FIG. 1A, except that one "surface" is formed by the ejected beads, in the absence of and substitution for that of the more distal balloon 3 (depicted in phantom) of FIG. 1A. Blood perfusion should not be blocked for a time interval exceeding that absolutely necessary to achieve such penetration, and in all events the interval of blockage should be capped at a limit that comfortably assures avoidance of damage to or ischemia of cells that may cause death of otherwise healthy tissue, resulting from the shortage of oxygen needed to meet the demand for cellular metabolism.

Referring now to FIG. 2, in one embodiment of a method for treating a tumor, oncolytic viruses within fluid carrier may be applied to the subject (patient) by initially introducing two-balloon catheter 11 into the vascular system, e.g., at the patient's groin using an introducer, and through a short guiding catheter 5 over a guide wire 18. The guide wire is inserted into the vascular system to a depth sufficient to accommodate advancement of the balloon catheter 11 over the guide wire via central lumen 12 of the catheter and into a blood vessel (an artery 8, in this example) or duct (as the case may be). The distal end of catheter 11 is advanced in proximity to the target site of the cancerous tissue (tumor 2) to receive the therapy to be provided by a method of the present invention. After such advancement of the catheter, guide wire 18 is then removed from the proximal end of the catheter via central lumen 12.

In the depicted example of FIG. 2, the tumor 2 is supplied with blood through artery 8 and its distal branches 9 and 10, etc., of the arterial tree. After the catheter is properly positioned as described above in the discussion of FIG. 1A, with at least a portion of tumor 2 situated between the more distal and more proximal balloons 14, respectively, the balloons are deployed by simultaneous inflation through an inflation lumen (not shown) to maintain the catheter's position within the artery. A combination of the effective dose of selected infecting oncolytic virus and pharmaceutically acceptable fluid carrier may then be injected under increasing pressure through an entry port at the proximal end of an infusion lumen 13 of the catheter 11 by hand injection or by means of a motor driven constant speed injection syringe (not shown). The virus and its fluid carrier are thereby discharged under pressure from one or more discharge port(s) of infusion lumen 13 located between the inflated balloons 14 bounding the target site of tumor 2 to receive treatment from the effective dose of virus delivered thereto.

The oncolytic virus particles 15 are thus delivered into the space occupied by the chamber formed at the target site by the confronting surfaces of the two balloons 14, the surface of catheter 11 and inner surface of vessel 8 therebetween. As the controlled pressure and volume of the virus particles and containment fluid in that space builds to a designated effective extravasation pressure, typically within a period of from 10 seconds to a few minutes, for example, the effective dose of infecting oncolytic virus particles of some 30 to 250 nm size is forced through the endothelial barrier at the inner lining of artery 8 bounding the target site and into the typically 10 μm entry holes of the defective cells of the tumor to destroy them or to allay their effect (e.g., place them in remission).

The disclosed delivery method overcomes several problems with prior vascular or ductal delivery schemes. During transit through the vascular system by a typical prior technique in which viruses are blood-borne, the viruses are susceptible to binding by antibodies that normally participate in deactivating viruses and removing them via the reticulo-endothelial system. Furthermore, any particles transiting a blood vessel or duct, including viruses, are normally separated from the parenchymatous organ or the tissue outside the vessel by the continuous cells lining the vascular or ductal conduit. Intravenously delivered oncolytic agents would be separated from the cancer tissue to be treated by the endothelial lining and other tissue layers of blood vessels that lead to the cancerous tissue. However, under circumstances produced by the methods of the present invention, virus delivery is through a catheter, and this endothelial barrier is overcome, to enable the virus to attach to the inner surface of the vessel, migrate and proliferate through the endothelial layer into the adjacent tissue. Here, an increase in pressure with increasing injection volume of the virus following balloon inflation defining the distribution zone (at the target site) can overcome the endothelial layer and effect extravasation from the vascular system and into the defective cancer cells to reduce or destroy the tumor or allay its effect as by remission.

The methods disclosed herein further provide for optimum numbers of the viral particles to contact and enter cells of the malignant tissue without dilution. Use of the two-balloon catheter 11 (or other mechanism such as the single balloon 4 of catheter 11A aided by the oppositely disposed bead wall 30 of FIG. 1B) allows for selective blockage of the antegrade blood flow and loss of the agent into the systemic circulation. Balloon catheters are preferred for use in methods of the present invention for reasons previously enumerated herein, and also because such catheters are well known, often used and reliable devices for introduction to a predetermined site in a vessel such as an artery or vein, or a duct. In the methods of the invention, the balloons 14 of catheter 11 are simultaneously inflated with biocompatible fluid through a separate inflation lumen of catheter 11 to occlude artery 8 and its distal branches 9, 10, etc. of its arterial tree, thereby causing perfusion through the vessel to cease. Inflation of the balloons may be commenced immediately before or at the time of injection of the oncolytic virus through the infusion lumen 13 of the catheter, and is maintained throughout the period of injection. This enables adhesion of a desired large number of infectious oncolytic viral agents to the target tissue.

Absence of blood flow at the delivery site has several advantageous effects. It prevents what would otherwise result in a retrograde loss of injected agents as well as antegrade dilution with blood flow, while providing a capability on the part of the physician or control instrumentation performing the method to increase the pressure at the injection site to an effective extravasation pressure to overcome the endothelial barrier and force the viruses into the sub-endothelial cells of the affected tissues.

Depending on location of the balloon(s), the type of vessel or duct, the type of organ to be treated, and the multiplicity of viral agents delivered, the blockage is maintained for a relatively short period of time, preferably on the order of one to fifteen minutes, and in any event sufficient to allow a high concentration and considerable number of viral attachments to defective cells of the cancer tissue (or other tissue of a disease or disorder) at the designated target site. In the case of a slow infusion of the oncolytic (or non-oncolytic) agents, the period of blockage is maintained longer by steady inflation of the balloon over the infusion period, for example up to about 30 minutes, for enhancement of contact and adherence to the endothelium. In the example of two-balloon catheter usage, both balloons are deflated simultaneously, and in any case, the balloon catheter is removed from the patient after the treatment procedure is completed.

The concepts of the present invention include using the natural distribution tree of the arterioles and the capillaries or the ductal distribution tree to cover the complete inner, medial and outer layers of the cancer tissue with oncolytic agents, or of affected tissue of other disease or disorder with non-oncolytic agents penetrating defective cells thereof.

The methods of the invention are not limited to treatment of a particular cancer, but rather, of various different types of cancer. For example, the method of treatment may be applied to brain cancer, e.g., glioma, in which case the infusion catheter is advanced to the site of the cancer tissue through an appropriate arterial path into the applicable region of the patient's brain, as described more fully below. Blockage of blood flow in this case would add a period (e.g., minutes) of limited blood supply but would enable the oncolytic agents to overcome the endothelial barrier.

Other possible cancers to be treated by the process disclosed herein include cancer of the pancreas, the liver, and the kidneys. The pancreas has a duct (the ductus Wirsungii) through which pancreatic enzymes are delivered into the intestines, and which can be accessed in a retrograde manner by endoscopic retrograde choledocho-pancreaticography (ERCP). By means of the visual guidance, such as through a small fiber optic instrument, a small balloon catheter may be introduced into this duct, and the balloon inflated to occlude the duct during delivery of oncolytic agents through the catheter's inner lumen to the site of the cancer tissue, so as to prevent the injected agents from being washed out into the intestines and thereby enhancing adhesion and penetration by a relatively large number of the administered agents. An analogous procedure may be used for treatment of cancerous tissue of the liver, through the bile duct system. Here also, it is important to overcome the barrier of the normal bile duct with pressure that can be generated only if the balloon is inflated while the agents are slowly injected. The pressure distal to the injection site increases as more and more volume is injected. Treatment of cancerous tissue in the kidney(s) may be conducted by an analogous procedure.

In an embodiment of the invention, effective delivery of the oncolytic viral agent may be visualized concurrently for accuracy of location in the subject's body. In one embodiment of delivery to the bile duct, intraoperative cholangiography is performed to visualize the anatomy of the duct system as well as effective delivery of the viral agent. In another embodiment, the viral agent is formulated with a dye such as a fluorescent dye that can be visualized such as with the same fiber optic guidance system that is used to introduce the balloon catheter into the duct or vessel. In one non-limiting example of a visualization system that may be employed, a dye visible at a wavelength of 750 nm or greater is used together with an exciting light source such as that as disclosed in U.S. Pat. No. 8,050,745, issued Nov. 1, 2011, incorporated herein by reference. Further examples of a visualization systems are disclosed in U.S. patent application Ser. No. 11/868,432, published as US 2008/0249400, and now abandoned, incorporated herein by reference. Other imaging methods include SPECT, CT and MRI together with their respective enhanced visualization agents.

Brain cancer: FIG. 3A is a transparent front view of a subject illustrating an exemplary procedure for injecting a prescribed quantity of virus contained in body-compatible fluid into the cerebral circulation of a patient, useful to describe an example of a method for delivery of oncolytic agents through a balloon-guided catheter to the anterior cerebral circulation in a patient 31. An introducer sheath 33 of appropriate size, typically 5-7 French, is advanced through the right groin 32. Then a two-balloon guided double lumen catheter 34 is advanced through introducer sheath 33 and over a small guide wire 48 directed to the artery of interest. Guide wire 48 has a diameter in a range of 0.014 to 0.018 inches, and a flexible distal tip to render it bendable so as to direct the guide wire through the vessel to the vicinity or locality of the selected target site. The proximal end of guide wire 48 is left to project from opening 35a of catheter 34. A side branch opening 35b of catheter 34 is operatively coupled through an inflation lumen of the catheter for selective simultaneous inflation and simultaneous deflation of its two balloons 46.

Initially, after guide wire 48 is advanced to its desired position, catheter 34 is inserted into the subject's vascular system and manoeuvred to the selected site by gliding it over the guide wire through the central lumen of the catheter. The distal end of the catheter may be advanced through iliac artery 37, abdominal and thoracic aorta 38, aortic arch 39, and into the right carotid artery 40 beyond the branching off of the vessels 41 for the right arm. As an alternative, guide wire 48 and catheter 34 may be advanced to a location in the left carotid artery 42. The left carotid artery either originates after the branch-off of the left subclavian artery 43, or directly from the aortic arch 39 where the left subclavian artery originates from a separate orifice in the aortic arch. After advancing catheter 34 through the common carotid artery into the right carotid artery 40 and into the proximal circulation of the circulus willisi 44, the anterior cerebral artery 45 is encountered at its origination. Alternatively, in lieu of access through the femoral artery, vascular access to the carotid may be obtained through the right radial artery, particularly in patients with a strong radial pulse.

After the catheter 34 has been advanced so that its distal tip 47 and two spaced-apart balloons 46 are positioned in the anterior cerebral artery 45, with tip 47 located such that the target site to which parvoviruses are to be delivered is situated between the two balloons, guide wire 48 is removed. The opening 35a of the same lumen that had been used for the guide wire is now available for injecting oncolytic agents, and that lumen is closed at the distal end of catheter 34 to open one or more discharge ports from the lumen into the space between the two balloons at the cerebral circulation. Toward that end, reference is now made also to FIGS. 3B and 3C, companion simplified views of syringes used in the course of the procedure shown and described with respect to FIG. 3A. The conus 50 of a syringe 49 (FIG. 3B) is connected to port 35a of catheter 34, and the conus 53 of another syringe 52 (FIG. 3C) is connected to the inflation port 35b of catheter 34. Port 35b opens through the inflation lumen for balloons 46 of catheter 34. Syringe 52 is typically of small size and includes a pressure gauge 55 to measure the applied pressure as the fluid 54 within the syringe is expelled into port 35b to inflate balloons 46 simultaneously to a low pressure of 0.5 to 0.8 atm. This pressure is sufficient to tightly seal the vessel (anterior cerebral artery 45) at the locations of the two balloons, and thereby block perfusion of blood between them. To assist in recognizing a possible rupture of either of balloons 46, the fluid 54 in syringe 52 may be a 50/50 mixture of saline and contrast dye. Balloons 46 may be deflated simultaneously at the completion of the procedure or in the event of an emergency by withdrawing the fluid 54 back into syringe 52.

While anterior cerebral artery 45 is tightly sealed at both its ends, oncolytic viral agents 51 within syringe 49 are slowly ejected from conus 50 into port 35a of the catheter 34. The oncolytic infecting viruses travel through the central lumen of catheter 34 formerly occupied by guide wire 48 and exit that lumen under pressure at the discharge port(s) between the inflated balloons and into the space of the chamber formed thereat, while blood perfusion is blocked in that part of the cerebral circulation. After a period in which the pressure builds as a result of the controlled volume and pressure of virus entering the chamber, an effective dose of the virus is delivered under an effective extravasation pressure for entry into the blocked cerebral circulation at that target site. The very brief period of limited blood supply during blockage of blood flow through the anterior cerebral artery 45 by the inflated balloons 46 and the pressure of the viral agents at that site is sufficient for the virus to overcome the endothelial barrier and enter the cancer cells in the underlying tissue, but not enough to cause injury to the brain. Repetitive injections with the allowance of intermittent blood flood may be employed as one means to increase the total virus delivered to affected tissue at the treatment site.

Renal cancer: For treating cancer of the kidneys, an oncolytic agent may be introduced in a similar manner through a two-balloon catheter navigated over a guide wire in the patient's right groin into the iliac artery 37, the abdominal aorta 38, the applicable renal artery 57, and the diseased kidney 58.

Figure 4:
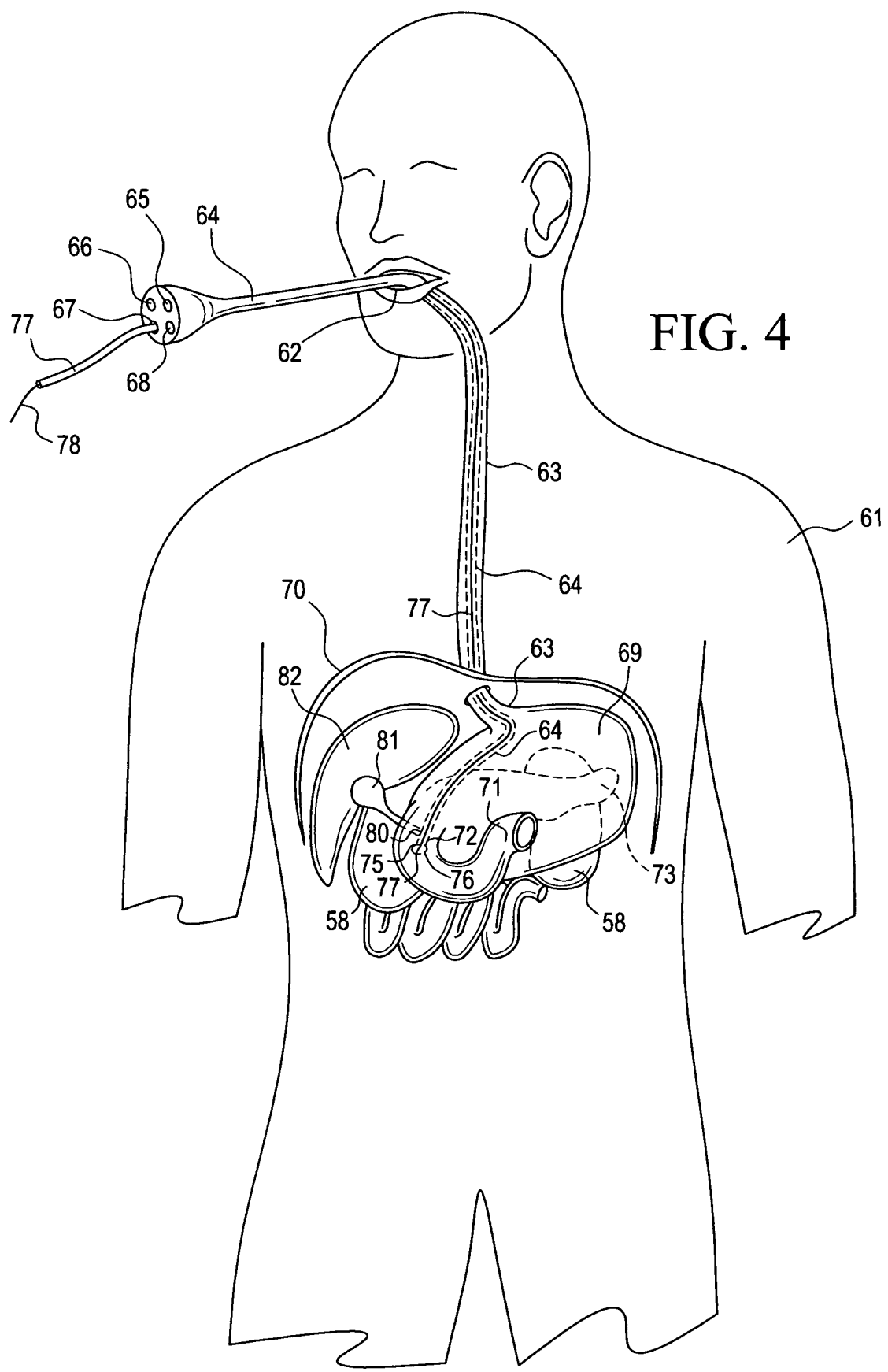
FIG. 4 is a transparent front view of a subject illustrating an exemplary procedure for administering a prescribed quantity of selected virus in body-compatible fluid intraluminally through a duct of the subject's body via a balloon catheter installed in the duct, to infect targeted tissue of the body attributable to or responsible for a disease or disorder under treatment.

Ductal Delivery: FIG. 4 is a transparent front view of a subject illustrating an exemplary procedure for administering a prescribed quantity of selected virus in body-compatible fluid intraluminally through a natural duct of the subject's body via a two-balloon catheter installed in the duct, to infect targeted tissue of the body attributable to or responsible for a disease or disorder under treatment. Referring to that Figure, in this exemplary initial procedure prior to delivery of treatment, an endoscope 64 is advanced through the mouth 62 and esophagus 63 of the patient 61. The endoscope 64 is flexible, and is designed and implemented with a plurality of channels including, in this illustrative embodiment, visualization and fiber optics channel 65, flushing channel 66, side port open channel 67, and working channel 68. The distal tip 75 of endoscope 64 is readily bendable to allow the endoscope to be advanced through a tortuous path. During the procedure the patient may be give a local anaesthetic to prevent gagging. The endoscope 64 is advanced via the esophagus 63 through the diaphragm 70, into and through the stomach 69, and further until its distal tip is located in the duodenum 71.

Pancreatic cancer: If the pancreas is target organ to be treated, the location of the distal tip should be such that a side port 72 (FIG. 4) of the endoscope adjacent its distal tip is aligned for entry into the ductus Wirsungii 76, which supports the internal structure of the pancreas 73 with all its side branches. Proper alignment may be verified through the visualization and fiber optics channel 65 of endoscope 64. Then, a small two-balloon guided catheter 77 (e.g., 2.7 French outer diameter) is advanced over a guide wire 78 threaded through the side port open channel 67 and out of the side port 72 into the ductus Wirsungii. Oncolytic viral agents are delivered and the balloon is inflated by the use of syringes in a method similar to that described with respect to FIGS. 3B and 3C. The distal tip of the catheter is advanced through channel 67 of the endoscope 64 and out of the side port 72 to the site of the pancreatic tissue to be treated. The catheter's two balloons are then inflated through the inflation lumen of the catheter to occlude the Wirsungii duct while oncolytic viruses in fluid carrier are introduced under pressure into the pancreatic tissue through an infusion lumen and discharge port(s) of the catheter between the spaced-apart inflated balloons. By proper positioning of the discharge port(s) at the site of the cancer tissue, an effective dose of the virus is delivered to the target site under an effective extravasation pressure locally in high concentration. Occlusion of the duct prevents the virus from washing out into the intestines, so as to enhance large scale adhesions and penetration of the virus into the target tissue.

Liver cancer: Blood enters the liver from both the hepatic artery and the hepatic portal vein. Oxygenated blood is carried via the hepatic artery into the sinusoids of the liver. Deoxygenated blood and nutrients from the digestive system are via the portal vein into the sinusoids of the liver, which are lined by plates of liver (hepatic) cells. Blood leaves the liver first through the sinusoids and into the central vein of each lobule before finally leaving the liver through the hepatic vein. Bile produced by the liver cells lining the sinusoids leaves the liver first through the bile canaliculi and ultimately through the bile duct. Thus, compounds delivered to the liver may be considered to be delivered with the normal direction of flow (antegrade) if delivered through the hepatic artery or the hepatic portal vein, and against the normal direction of flow (retrograde) if delivered through the hepatic vein or through the bile duct. Retrograde delivery through the bile duct can be accomplished endoscopically as is done with contrast dyes in ERCP procedures or percutaneously as in PTCA procedures (Percutaneous Transhepatic Cholangiography).

As depicted in FIG. 4, for retrograde ductal delivery, the distal tip 75 of endoscope 64 is positioned in the duodenum 71 such that its side port 72 is aligned for entry into the common biliary duct 80, which supports the liver 82 and the gall bladder 81. As an alternative, the side branch of the bile duct may be used. The guide wire and balloon catheter are fed through channel 67 and out of side port 72 of the endoscope, into the duct. The distal tip of the catheter is positioned at the target site of the liver tissue, the guide wire is removed, and the catheter's balloon is inflated to occlude the biliary duct during the introduction of the virus. The oncolytic viruses are injected through the infusion lumen and ejected from its discharge port(s) of the catheter for adhesion to and engraftment within or in proximity to the tumor.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements and that the invention shall be limited only by the appended claims and the rules and principles of applicable law.

What is claimed is:

1. A method for treating a disease or disorder in the body of a subject by delivering effectively and with high concentration a selected virus locally to affected tissue at a target site of defective cells of the body representative of the disease or disorder to be treated, the method including selecting the virus for its ability to infect the defective cells in the affected tissue so as to allay the defect therein while leaving normal cells unscathed; selecting a balloon catheter sized for advancement to the target site through a blood vessel or fluid duct of the subject's body in direct fluid communication with the target site, said balloon catheter having a discharge port of an infusion lumen situated between two spaced-apart inflatable balloons coupled by an inflation lumen of the balloon catheter; advancing the balloon catheter through the vessel or fluid duct to position its distal end such that the target site is located between the two balloons, and inflating both balloons through the inflation lumen to maintain the balloon catheter so positioned with the discharge port confronting the target site, thereby (i) forming an open space encompassed by the lining of the vessel or fluid duct, the outer surface of the balloon catheter, and confronting surfaces of the two inflated balloons, and (ii) blocking normal perfusion through the vessel or fluid duct within the open space; transluminally infusing a therapeutically effective dose of the virus in containment fluid for discharge into said open space through the infusion lumen and the discharge port of the infusion lumen; and selectively increasing pressure of the discharged virus by increasing the volume of fluid containing the virus in said open space, to force the virus under an effective extravasation pressure through the natural endothelial barrier of the lining of the vessel or fluid duct within said open space, without removing or otherwise injuring the endothelial barrier, and into the defective cells of the affected tissue beneath the endothelial barrier at the target site, sufficient for delivery of the effective dose of the virus thereto.

2. The method of claim 1, wherein the disease or disorder to be treated is cancer, the affected tissue is a malignant tumor, the selected virus is an oncolytic virus, and the therapeutically effective dose of the virus is contained within a pharmaceutically acceptable fluid carrier constituting the containment fluid.

3. The method of claim 1, wherein the disease or disorder to be treated is attributable to single-gene defects for treatment by somatic cell gene therapy, the affected tissue is selected from one of an immunodeficiency, cystic fibrosis, hemophilia, muscular dystrophy, and sickle cell anemia, the selected virus is an engineered non-oncolytic virus having incorporated therein therapeutic DNA integrated into its genome for delivery into a chromosome so as to administer a gene that causes expression of a needed protein and thereby replace or disrupt the defective gene to treat the disease or disorder.

4. A method for treating a disease or disorder in the body of a subject, said method comprising the steps of occluding a blood vessel or duct of the body bounding a target site of defective cells of affected tissue of the disease or disorder with two spaced-apart balloons of a balloon catheter inflated to create a chamber therebetween at the target site and to block normal perfusion through the vessel or duct at the chamber, infusing an effective dose of a virus selected for its ability to infect and thereby treat the defective cells and contained in a body-compatible fluid carrier under pressure through an infusion lumen of the balloon catheter and into the chamber, and controlling the volume of the selected virus and said body-compatible fluid carrier delivered into the chamber and thereby the pressure therein so as to reach an effective extravasation pressure sufficient to force the effective dose of the virus through a natural endothelial barrier lining the vessel or duct within the chamber, without inflicting damage thereto, to penetrate the endothelial barrier and induce a desired therapeutic effect in defective cells of the affected tissue in the vicinity of the target site.

5. The method of claim 4, wherein the disease or disorder to be treated is cancer, the affected tissue is a malignant tumor, the selected virus is an oncolytic virus, and delivery of the virus into the chamber is performed by infusing the effective dose thereof in a pharmaceutically acceptable fluid carrier constituting said body-compatible fluid carrier through the infusion lumen of the balloon catheter inserted in the vessel or duct to position the chamber at the target site.

6. The method of claim 4, wherein the disease or disorder to be treated is attributable to single-gene defects for treatment by somatic cell gene therapy, the affected tissue is from one of an immunodeficiency, cystic fibrosis, hemophilia, muscular dystrophy, and sickle cell anemia, the selected virus is an engineered non-oncolytic virus having incorporated therein therapeutic DNA integrated into its genome for delivery into a chromosome so as to administer a gene that causes expression of a needed protein and thereby replace or disrupt the defective gene in cells of the affected tissue in the vicinity of the target site.

7. The method of claim 4, wherein the disease or disorder to be treated is attributable to a gene defect for treatment by gene therapy, the affected tissue is from one of an acquired or inborn disease including HIV, immunodeficiency, cystic fibrosis, hemophilia, muscular dystrophy, or sickle cell anemia, the selected virus is an engineered non-oncolytic virus having the ability to induce therapeutic RNA, mRNA, iRNA, shRNA, DNA, or CRISPR Cas9 constructs, integrated into its genome for delivery into the chamber for penetration of cells of the affected tissue in proximity to the target site so as to induce a genetic modification that causes expression of a needed protein to modify, replace or disrupt the defective gene in the penetrated cells.

* * * * *